US011076758B2

(12) United States Patent
Kozloski et al.

(10) Patent No.: US 11,076,758 B2
(45) Date of Patent: Aug. 3, 2021

(54) CONTROLLING DEVICES BASED ON PHYSIOLOGICAL MEASUREMENTS

(71) Applicant: International Business Machines Corporation, Armonk, NY (US)

(72) Inventors: James Robert Kozloski, New Fairfield, CT (US); Mauro Marzorati, Lutz, FL (US); Brian Marshall O'Connell, Research Triangle Park, NC (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 669 days.

(21) Appl. No.: 15/246,998

(22) Filed: Aug. 25, 2016

(65) Prior Publication Data

US 2016/0363334 A1 Dec. 15, 2016

Related U.S. Application Data

(63) Continuation of application No. 13/277,901, filed on Oct. 20, 2011, now Pat. No. 9,504,386.

(51) Int. Cl.
*G05B 13/00* (2006.01)
*A61B 5/00* (2006.01)
(Continued)

(52) U.S. Cl.
CPC .............. *A61B 5/00* (2013.01); *A61B 5/0205* (2013.01); *A61B 5/389* (2021.01); *F24F 11/30* (2018.01);
(Continued)

(58) Field of Classification Search
CPC .......... F24F 2221/38; F24F 2120/12–2120/14; F24F 210/00; G05B 2219/2614;
(Continued)

(56) References Cited

U.S. PATENT DOCUMENTS 5,145,112 A 9/1992 Ueda
5,170,935 A * 12/1992 Federspiel ......... G05D 23/1902
236/44 C
(Continued)

FOREIGN PATENT DOCUMENTS

JP 59140117 8/1984
JP 61099044 5/1986
(Continued)

OTHER PUBLICATIONS

Wettschereck, D. et al.; "A Review and Empirical Evaluation of Feature Weighting Methods for a Class of Lazy Learning Algorithms"; Artificial Intelligence Review 11: 273-314, 1997 (Year: 1997).*

(Continued)

*Primary Examiner* — Lori A. Clow
*Assistant Examiner* — Marie Archer
(74) *Attorney, Agent, or Firm* — Fleit Intellectual Property Law; Jose Gutman

(57) ABSTRACT

Embodiments of the invention control a device based on physiological measurements associated with a user. A determination is made that a user has manually adjusted a controlled device. A context associated with the user is identified in response to determining that the user has manually adjusted the controlled device. A change is detected in at least one physiological measurement associated with the user in response to the controlled device being manually adjusted. A target physiological measurement associated with at least one physiological measurement is modified based on the change that has been detected. The context that has been identified is associated with the target physiological measurement that has been modified.

14 Claims, 7 Drawing Sheets

(51) Int. Cl.

| | | |
|---|---|---|
| *H04L 12/28* | (2006.01) | |
| *F24F 11/30* | (2018.01) | |
| *G16H 40/63* | (2018.01) | |
| *G16H 40/67* | (2018.01) | |
| *A61B 5/389* | (2021.01) | |
| *A61B 5/0205* | (2006.01) | |
| *G05B 19/409* | (2006.01) | |
| *G06Q 10/10* | (2012.01) | |
| *F24F 140/60* | (2018.01) | |
| *F24F 110/00* | (2018.01) | |
| *A61B 5/024* | (2006.01) | |
| *A61B 5/0533* | (2021.01) | |
| *A61B 5/08* | (2006.01) | |

(52) U.S. Cl.
CPC ....... *G05B 19/409* (2013.01); *G06Q 10/1093* (2013.01); *G16H 40/63* (2018.01); *G16H 40/67* (2018.01); *H04L 12/282* (2013.01); *H04L 12/2803* (2013.01); *H04L 12/2816* (2013.01); *A61B 5/024* (2013.01); *A61B 5/0533* (2013.01); *A61B 5/08* (2013.01); *A61B 2560/0242* (2013.01); *F24F 2110/00* (2018.01); *F24F 2140/60* (2018.01); *G05B 2219/2614* (2013.01); *G05B 2219/40585* (2013.01)

(58) Field of Classification Search
CPC ...... G05D 23/1931; G06N 5/04–5/048; H04L 12/282; Y02B 30/00–30/90; A01K 1/0052
See application file for complete search history.

(56) References Cited

U.S. PATENT DOCUMENTS

| | | | |
|---|---|---|---|
| 5,172,856 A | 12/1992 | Tanaka et al. | |
| 6,182,022 B1* | 1/2001 | Mayle | G06F 11/3409 |
| | | | 702/182 |
| 7,188,668 B2 | 3/2007 | Hara et al. | |
| 7,386,863 B2* | 6/2008 | Bodin | H04L 12/2803 |
| | | | 709/223 |
| 8,388,530 B2 | 3/2013 | Shusterman | 600/300 |
| 2002/0010390 A1 | 1/2002 | Guice et al. | |
| 2003/0052789 A1* | 3/2003 | Colmenarez | G06K 9/00771 |
| | | | 340/575 |
| 2003/0060728 A1 | 3/2003 | Mandigo | |
| 2003/0080728 A1 | 3/2003 | Mandigo | |
| 2003/0208110 A1 | 11/2003 | Mault et al. | |
| 2005/0124900 A1* | 6/2005 | Stadler | A61B 5/0031 |
| | | | 600/509 |
| 2005/0209061 A1 | 9/2005 | Crawford et al. | 482/54 |
| 2006/0031102 A1* | 2/2006 | Teller | A61B 5/411 |
| | | | 705/3 |
| 2006/0142968 A1 | 6/2006 | Han et al. | 702/120 |
| 2007/0070038 A1 | 3/2007 | Hoffberg et al. | 345/156 |
| 2007/0168229 A1 | 7/2007 | Kim | 705/2 |
| 2007/0265533 A1 | 11/2007 | Tran | |
| 2008/0033252 A1 | 2/2008 | Estrella | 600/300 |
| 2008/0191045 A1* | 8/2008 | Harter | G05D 23/1904 |
| | | | 236/91 D |
| 2008/0287751 A1 | 11/2008 | Stivoric et al. | 600/301 |
| 2008/0297336 A1 | 12/2008 | Lee | |
| 2009/0030555 A1* | 1/2009 | Gray | F24F 11/30 |
| | | | 700/277 |
| 2009/0253554 A1 | 10/2009 | McIntosh | 482/4 |
| 2009/0318779 A1 | 12/2009 | Tran | 600/301 |
| 2010/0036533 A1 | 2/2010 | Masuda et al. | 700/278 |
| 2010/0080431 A1 | 4/2010 | Datema et al. | |
| 2010/0130833 A1 | 5/2010 | Mott et al. | 600/300 |
| 2010/0262298 A1* | 10/2010 | Johnson | F24F 11/001 |
| | | | 700/277 |
| 2010/0268051 A1 | 10/2010 | Prasad et al. | 600/365 |
| 2010/0289643 A1 | 11/2010 | Trundle et al. | 340/545.1 |
| 2010/0324376 A1 | 12/2010 | Chinnadural et al. | 600/300 |
| 2011/0010014 A1 | 1/2011 | Oexman et al. | 700/276 |
| 2011/0066465 A1 | 3/2011 | Orfield | 705/7.32 |
| 2011/0237905 A1 | 9/2011 | Kutzik et al. | 600/300 |
| 2012/0041278 A1 | 2/2012 | Sadhu | 600/301 |
| 2012/0064818 A1 | 3/2012 | Kurelowech | 454/251 |
| 2012/0066168 A1* | 3/2012 | Fadell | G06N 5/048 |
| | | | 706/52 |
| 2012/0072032 A1 | 3/2012 | Powell et al. | 700/278 |

FOREIGN PATENT DOCUMENTS

| | | |
|---|---|---|
| JP | 4945342 | 2/1992 |
| JP | 5033204 | 2/1993 |
| JP | 5322262 | 12/1993 |
| JP | 2004125376 | 4/2004 |
| JP | 2006138606 | 6/2006 |
| JP | 4045342 | 2/2008 |
| JP | 2008121963 | 5/2008 |

OTHER PUBLICATIONS

J. Liang, R. Du; "Design of intelligent comfort control system with human learning and minimum power control strategies"; Energy Conversion and Management, vol. 49, Issue 4, 2008, pp. 517-528. (Year: 2008).*

Federspiel, C. C., and Asada, H. (Sep. 1, 1994). "User-Adaptable Comfort Control for HVAC Systems." ASME. J. Dyn. Sys., Meas., Control. Sep. 1994; 116(3): 474-486. (Year: 1994).*

International Search Report and Written Opinion dated Dec. 28, 2012 for PCT/US12/60933.

* cited by examiner

FIG. 2

| Heart Rate ~202 | Muscle ~206 | Skin Conductance ~210 | Respiration ~214 |
|---|---|---|---|
| Range_A 204 | Range_B 208 | Range_C 212 | Range_D 216 |
| ... | ... | ... | ... |

| Context ~302 | Heart Rate | Muscle | Skin Conductance | Respiration |
|---|---|---|---|---|
| Context_1 304 | Range_A 306 | Range_B 308 | Range_E 310 | Range_D 312 |
| N/A 316 | Range_A 318 | Range_B 320 | Range_C 322 | Range_D 324 |
| ... | ... | ... | ... | ... |
| Context_N | Range_F | Range_G | Range_H | Range_I |

300

314 ↗ (pointing to N/A 316 row)
326 ↗ (pointing to row 316-324)

CONTROLLING DEVICES BASED ON PHYSIOLOGICAL MEASUREMENTS

BACKGROUND

The present invention generally relates to physiological measurements, and more particularly relates to controlling devices based on physiological measurements.

Manufacturers of environmental devices such as HVAC (heating, ventilating, and air conditioning) equipment are attempting to make the systems they manufacture more efficient. Efficiency requirements are driven by rising energy costs, and have more recently been driven by increased awareness of environmental issues. There are several methods for making HVAC systems more efficient. One method for achieving energy efficiency in central HVAC systems is by introducing zones that are controlled by multiple thermostats. This allows a more granular application of heat, similar to non-central heating systems. The rationale behind this method is avoiding the expense of heating or cooling in unneeded zones or areas. Another method is to employ heat exchangers to recover sensible or latent heat from exhausted air. This is done by transfer of energy to the incoming outside fresh air. The rationale behind this method is also avoidance, namely reducing the amount of time the system is actively working. However, conventional methods for controlling environmental devices are generally based on temperature readings, timers, and/or user activation signals. This can lead to the inefficient and over-use of the devices.

BRIEF SUMMARY

In one embodiment, a method for controlling a device based on physiological measurements associated with at least one user is disclosed. The method includes determining that a user has manually adjusted a controlled device. A context associated with the user is identified in response to determining that the user has manually adjusted the controlled device. A change is detected in at least one physiological measurement associated with the user in response to the controlled device being manually adjusted. A target physiological measurement associated with at least one physiological measurement is modified based on the change that has been detected. The context that has been identified is associated with the target physiological measurement that has been modified.

In another embodiment, a system for controlling a device based on physiological measurements associated with at least one user is disclosed. The system includes memory, a processor that is communicatively coupled to the memory. A controlling system is communicatively coupled to the memory and the processor. The controlling system is configured to perform a method. The method includes determining that a user has manually adjusted a controlled device. A context associated with the user is identified in response to determining that the user has manually adjusted the controlled device. A change is detected in at least one physiological measurement associated with the user in response to the controlled device being manually adjusted. A target physiological measurement associated with at least one physiological measurement is modified based on the change that has been detected. The context that has been identified is associated with the target physiological measurement that has been modified.

In yet another embodiment a computer program product is disclosed. The computer product is embodies computer readable non-transitory instructions which, when implemented, cause a computer to carry out the steps of a method for controlling a device based on physiological measurements associated with a user. The method includes determining that a user has manually adjusted a controlled device. A context associated with the user is identified in response to determining that the user has manually adjusted the controlled device. A change is detected in at least one physiological measurement associated with the user in response to the controlled device being manually adjusted. A target physiological measurement associated with at least one physiological measurement is modified based on the change that has been detected. The context that has been identified is associated with the target physiological measurement that has been modified.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIG. 2 shows a table comprising target physiological measurements according to one embodiment of the present invention;

FIG. 3 shows a table comprising target physiological measurements that are modified based on a context associated with a user according to one embodiment of the present invention;

DETAILED DESCRIPTION

Figure 1:
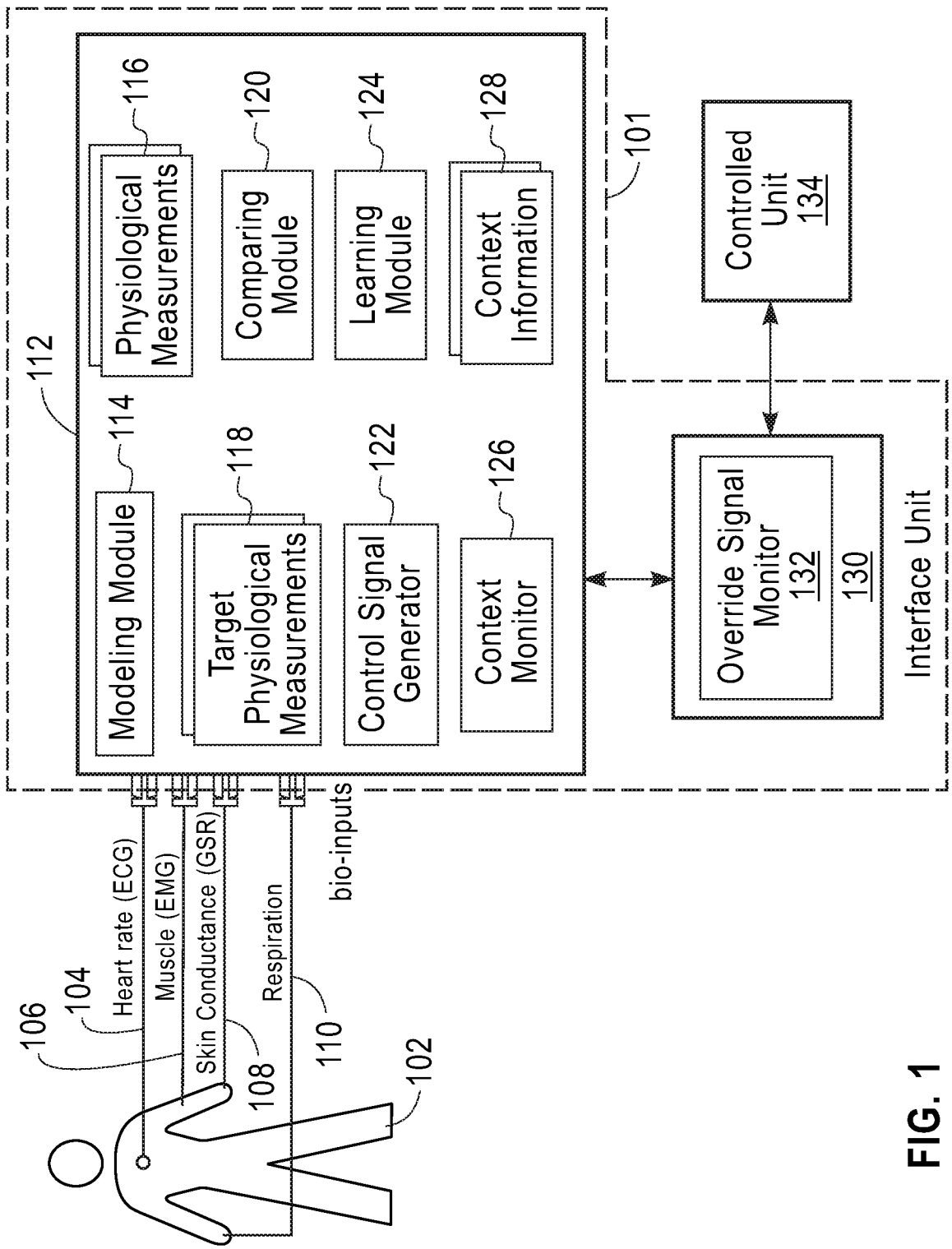
FIG. 1 is a block diagram illustrating one example of an operating environment for controlling devices based on physiological measurements associated with one or more users according to one embodiment of the present invention.

FIG. 1 shows one example of an operating environment 100 applicable to various embodiments of the present invention. The operating environment 100, in one embodiment, includes one or more users 102 each coupled to at least one physiological response monitor (PRM) 104, 106, 108, 110. A PRM 104, 106, 108, 110 is a device that is able to measure the physiological response of humans (or animals) with respect to one or more environmental factors such as, but not limited to, temperature, humidity, pressure, air quality, etc.

For example, FIG. 1 shows that a PRM can be a heart rate monitor 104 such as an electrocardiography (ECG) device, a muscle monitor 106 such as an electromyography (EMG) device, a skin conductance monitor 108 such as a galvanic skin response (GSR) device, and a respiration monitor 110. It should be noted that even though FIG. 1 shows these physiological response monitors as being separate, two or more of these monitors can reside on a single device.

A PRM 104, 106, 108, 110 can be coupled to a user 102 in various ways. For example, a PRM can include electrically conductive contact bands that form an electrical circuit and contact the skin of the user 102. In another embodiment, a computer pointing device such as a mouse or trackball can include conductive contact points that contact a user's hand or fingers. Each PRM 104, 106, 108, 110 is communicatively coupled to a PRM controller 112 via wired and/or wireless communication mechanisms. The PRM controller 112 is a device that manages and controls one or more PRM devices 104, 106, 108, 110. In one embodiment the PRM controller 112 communicates (either by wireless or wired communication mechanisms) with one or more PRM devices 104, 106, 108, 110 via a reliable protocol such as, but not limited to, the WebSphere® MQ Telemetry Transport protocol. This allows the PRM controller 112 to receive and collect signals (e.g., bio input) from the PRMs 104, 106, 108, 110. The WebSphere® MQ Telemetry Transport protocol is a lightweight publish/subscribe protocol flowing over TCP/IP for remote sensors and control devices through low bandwidth communications. This protocol is used by specialized applications on small footprint devices that require a low bandwidth communication, typically for remote data acquisition and process control.

In one embodiment, the PRM controller 112, in one embodiment, includes a modeling module 114, received (and optionally modeled) physiological measurements 116, target physiological measurements 118, a comparing module 120, control signal generator 122, a learning module 124, a context monitor 126, and context information 128. Each of these components is discussed in greater detail below. The PRM controller 112 is communicatively coupled to an interface unit 130, which interfaces directly with a controlled device 134 such as, but not limited to an HVAC system. The interface unit 130 includes an override signal monitor 132, which is discussed in greater detail below. The PRM controller 112 and the interface unit 130 are collectively referred to as the "control system 101". It should be noted that even though the PRM controller 112 and the interface unit 130 are shown as separate components then can also be disposed within a single unit as well.

The interface unit 130, in one embodiment, can be coupled to or replace the activating module, such as a thermostat, of the controlled device 134. In other words, the interface unit 130 provides the input necessary to establish if and how the controlled device 134 should be activated/deactivated and operated. For example, if the controlled device 134 is an HVAC system, the interface unit 130 provides the input that indicates whether the HVAC system is to heat, cool, turn off, etc. In one embodiment the interface unit 130 replaces the thermometer as the main sensor to a given thermostat. In this embodiment the interface unit 130 is electrically connected to the thermostat and closes the circuit whenever sufficient signals from the PRM controller 112 indicate that the HVAC system should be in operation. In another embodiment the interface unit 130 is installed as an additional sensing device to complement existing sensors that may be used to control device 134. It should be noted that even though an HVAC system is used as one example of a controlled device, the following discussion is also applicable to other devices such as, but not limited to, lighting devices, water devices, cleaning devices, personal hygiene devices, entertainment devices, and any other controllable devices.

The following is a more detailed discussion on controlling devices based on physiological measurements associated with one or more users 102. As discussed above, the PRMs 104, 106, 108, 110 generate physiological measurements associated with a user 102 and can also measure and record ambient temperature as well. For example, with respect to a GSR monitor 108, an electrical current can be generated along the contact bands or contacts points of the monitor 108 so that the resistance of the circuit in contact with the user's skin can be measured over time. These measurements are recorded along with a time-stamp.

The recorded physiological measurements, time-stamps, and any environmental information is then transmitted from the PRMs 104, 106, 108, 110 to the PRM controller 112 via wireless or wired communication mechanisms. The modeling module 114 of the PRM controller 112 then optionally models the physiological measurements received as input from the PRMs 104, 106, 108, 110. The PRM controller 112 utilizes one or more filters such as, but not limited to, a Kalman filter to perform the modeling. This filter utilizes measurements observed over time, which can contain random variations (i.e., noise) and other inaccuracies, and produces values that are closer to the true values of the measurements and their associated calculated values.

The comparing module 120 of the PRM controller 112 then compares the received (or modeled) physiological measurements 116 to one or more target physiological measurements 118 for determining a current state (e.g., comfort level) of the user 102 with respect to one or more environmental factors such as temperature, humidity, etc. For example, the PRM controller 112 based on this comparison is able to determine whether the user 102 is hot, cold, dehydrated, stressed, etc.

The target physiological measurements 118, in one embodiment, are sets of information that identify target measurements values, ranges of measurement values, and/or measurement value thresholds associated with a given user 102. A target physiological measurement can also be a time-varying function of a physiological measurement. This allows the PRM controller 112 to adjust for a measurement that may not be achievable. For example, the PRM controller 112 is able to target a "decreasing respiration rate" in general, without forcing the system to attempt to achieve "30 breaths/minute" exclusively.

One of the goals of the control system 101 is to maintain the physiological measurements of the user 102 within a target physiological measurement for one or more of physiological measurement categories. FIG. 2 shows a table 200 comprising target physiological measurements for a given user with respect to one or more physiological measurement categories such as heart rate, muscle electrical activity, skin conductance, and respiration.

In particular, FIG. 2 shows a first column 202 entitled "Heart Rate". This column 202 includes one or more entries 204 identifying a targeted heart rate for the user 102. In the example of FIG. 2, the targeted heart rate is a range of heart rates represented as Range_A. A second column 206 entitled "Muscle" includes one or more entries 208 identifying a targeted electrical activity of the user's muscles. In this example, the targeted electrical activity is a range of electrical activity represented as Range_B. A third column 210 entitled "Skin Conductance" includes one or more entries 212 identifying a targeted skin conductance for the user. In this example, the targeted skin conductance is a range of skin conductance levels represented as Range_C. A fourth column 214 entitled "Respiration" includes one or more entries 216 identifying a targeted respiration level for the user. In this example, the targeted respiration level is a range of respiration levels represented as Range_D. It should be noted that a target physiological measurement is not limited to being a range of measurements/levels and can be a specific measurement/level or a threshold as well.

When the PRM controller 112 receives the physiological measurements 116 from the PRMs 104, 106, 108, 110 or after the modeling process discussed above, the comparing module 120 analyzes the target physiological measurements 118 (shown in FIG. 2) to identify target physiological measurements associated with the received (or modeled) physiological measurements. For example, if the PRM controller 112 receives GSR measurements the comparing module 120 analyzes the target physiological measurement information 118 to identify the corresponding target physiological measurement, which is Range_C in this example.

The comparing module 120 then compares the received (or modeled) GSR physiological measurement to the corresponding target physiological measurement of Range_C to determine if the received (or modeled) GSR physiological measurement is within the target Range_C. If the received (or modeled) GSR physiological measurement is within the target Range_C then the PRM controller 112 does not send a control signal over to the interface unit 130. However, if the received (or modeled) GSR physiological measurement fails to be within the target Range_C, the control signal generator 122 generates one or more control signals for activating, deactivating, and/or changing one or more operating parameters/conditions of the controlled device 134 in order to bring the one or more physiological measurements of the user 102 within the target range.

The generated control signals can be based on whether the received (or modeled) physiological measurement(s) are above or below the corresponding target physiological measurement(s) 118. In another embodiment, type of control signals generated can be based on the delta between the received (or modeled) physiological measurement(s) and the corresponding target physiological measurement(s) 118. For example, the received (or modeled) GSR physiological measurement(s) being above the corresponding GSR target physiological measurement can indicate that the user 102 is hot. Therefore, the PRM controller 112 identifies a current state of the controlled device 134, which can be off, on, etc., and also identifies any operating parameters such as temperature settings and fan speed settings. If the controlled device 134 is currently operating, the PRM controller 112, via the control signal generator 122, can generate one or more control signals that decrease the temperature setting of the controlled device 134 and optionally adjust the speed to the fan. Alternatively, if the current operating mode is set to Heat the PRM controller 112 can generate a control signal that turns of the controlled device 134 or changes the operating mode to A/C with a temperature setting that is below the current ambient temperature of the room.

If the controlled device 134 is not currently operating, the PRM controller 112, via the control signal generator 130, can generate one or more control signals to turn on the controlled device 134 and change the temperature and/or fan speed settings if necessary. If the current operating mode of the controlled device 134 is set to Heat, a control signal can be generated to change the operating mode to A/C. If the current temperature setting is above the ambient temperature of the room, the PRM controller 112 can generate a control signal to decrease the temperature setting of the controlled device and optionally adjust the speed of the fan.

In another example, the received (or modeled) GSR physiological measurement(s) being below the target physiological measurement can indicate that the user 102 is cold. Therefore, the PRM controller 112 identifies a current state of the controlled device 134, which can be off, on, etc., and also identifies any operating parameters such as temperature settings and fan speed settings. If the controlled device 134 is currently operating, the PRM controller 112, via the control signal generator 130, can generate one or more control signals that increase the temperature setting of the controlled device 134 and optionally adjust the speed to the fan. Alternatively, if the current operating mode is set to A/C the PRM controller 112 can generate a control signal that turns of the controlled device 134 or changes the operating mode to Heat with a temperature setting that is above the current ambient temperature of the room.

If the controlled device 134 is not currently operating, the PRM controller 112, via the control signal generator 130, can generate one or more control signals to turn on the controlled device 134 and change the temperature and/or fan speed settings if necessary. If the current operating mode of the controlled device 134 is set to A/C, a control signal can be generated to change the operating mode to Heat. If the current temperature setting is below the ambient temperature of the room, the PRM controller 112 can generate a control signal to increase the temperature setting of the controlled device and optionally adjust the speed of the fan. It should be noted that control signals with other types of functions can also be generated as well. It should also be noted that the above comparing and adjusting (control signal generating) processes can also be based on a combination of physiological measurements as well. The generated control signals are then transmitted by the PRM controller 112 to the interface unit 130. The interface unit 130 then operates the controlled device 134 according to the received control signals.

As the PRM controller 112 continues to receive physiological measurement(s) from the PRMs 104, 108, 106, 110, the above comparison process is performed. When the PRM controller 112 determines that the received (or modeled) physiological measurement(s) substantially matches the corresponding target physiological measurement(s) 118 the controlled device 134 can be deactivated, returned to a previous operating state, and/or have one or more operating parameters modified. The above comparing and adjusting processes are then continued for maintaining the physiological measurements of the user within the corresponding target physiological measurements 118.

Figure 8:
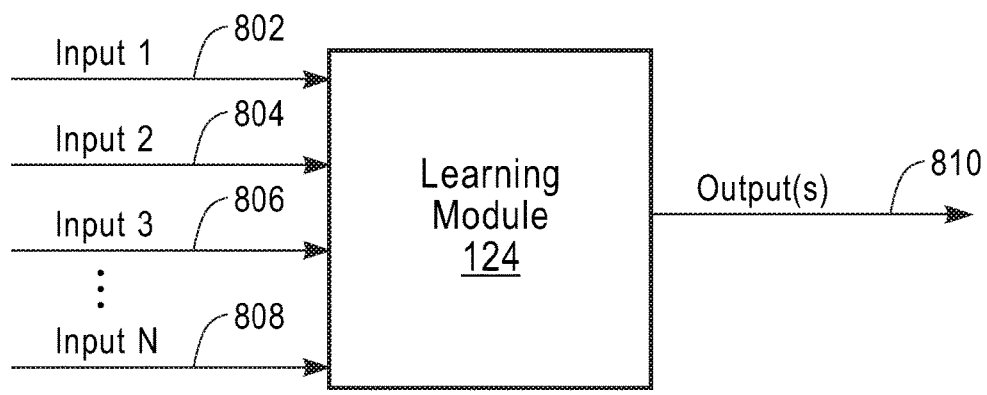
FIG. 8 is a block diagram illustrating inputs and outputs of a learning module according to one embodiment of the present invention and FIG. 9 illustrates one example of an information processing system according to one embodiment of the present invention.

In another embodiment, the PRM controller 112 utilizes the learning module 124 to modify the target physiological measurements 118 based on one or more inputs received by the learning module 124. For example, FIG. 8 shows that the learning module 124 receives one or more inputs 802, 804, 806, 808 such as controlled device parameters, one or more contextual inputs, override input, and user measurements. Controlled device parameters can be, for example, a current device parameter setting such as a current temperature setting of an A/C device, a desired setting as indicated by the PRM controller 112 and/or a user, and or the like.

Contextual inputs can be, for example, environmental factors, user activity information, scheduling information, and the like. For example, environmental factors can be, but are not limited to, current time or time of day (e.g., morning, afternoon, evening, etc.), weather conditions, and the like. User activity information can be for example, information identifying a current activity being performed (or having been completed) by the user as, but not limited to, exercising, taking a shower, sleeping, etc. Scheduling information can be information taken from, for example, a calendar program. Override input information can be, for example, an override signal generated by the user in response to the PRM controller 112 activating, deactivating, failing to activate, and/or changing one or more parameters of the controlled device 134. Measurement information can be, for example, the physiological measurement(s) discussed above.

The PRM controller 112 utilizes these multiple inputs to determine target physiological measurements for a given context. For example, the learning module 124 can determine from a plurality of inputs that the user changed the current A/C temperature from 88 degrees (as set of the PRM controller 112) to 84 degrees after the user finished jogging and while the humidity in the house was 45%. Based on these inputs the learning module 124 generates a signal(s) 810 for modifying target physiological measurements 118 accordingly. The learning module 124 can also generate one or more signals 810 that automatically modify one or more operating parameters of the controlled device 134 based on the received input(s) to achieve the target physiological measurements 118.

In one embodiment, the learning module 124 uses a supervised learning algorithm to learn over time. However, other learning methods are applicable as well. This learning aspect of the learning module 124 allows the PRM controller 112 to automatically and dynamically adjust target physiological measurements and/or controlled device operating parameters based on the received inputs 802, 804, 806, 808 discussed above. This is advantageous because the user 102 may desire a different target physiological measurement for one or more physiological measurements based on different contexts such as, but not limited to, time of day, user activity, calendar information, and the like. For example, after working outdoors the user 102 may want a physiological measurement(s) to be at a value below the corresponding target physiological measurement(s) 118. However, at nighttime the user 102 may want the same physiological measurement(s) to be above the target physiological measurement(s) 118. Based on the learning process performed by the learning module 124 to PRM controller 112 can automatically adjust the target physiological measurements and/or the controlled device 134 to keep the user at a given comfort level.

In one embodiment, the user 102 will typically override the control system 101 and manually adjust the operating parameters of the controlled advice 104 to achieve the physiological measurement(s), which relates to a comfort level desired by the user. For example, after working outdoors the user 102 may feel hotter than usual. Therefore, the user 102 manually adjusts the controlled device 134 to emit cooler air than what the system is currently set for. When the user 102 manually adjusts (e.g., overrides the control system 101) the controlled device 134, the override signal monitor 132 of the interface unit 130 detects this user override. The interface unit 130 then sends a signal(s) to the PRM controller 112 notifying the controller of the override. This signal(s) can also include any operating parameters such as operating mode, operating temperature, fan speed, etc. set by the user 102 and the time of day that the override was performed. This signal and any related information is also received by the learning module 124 as an input.

When the PRM controller 112 receives this signal from the interface unit 130, the context monitor 126 determines a current context such as a time of day, an activity performed or being performed by the user 102, etc. A context can be determined based on information received from clock, calendar software, global positioning satellite devices, various activity (or other) sensors such as an pedometer, etc. that are communicatively coupled to the PRM controller 112. This information can also be entered directly into the PRM controller 112 or a PRM 104, 106, 108, 110 by the user 102. The determined/identified context 128 is then stored at the PRM controller 112 and/or sent to the learning module 124 as an input(s).

The learning module 124 of the PRM controller 112 analyzes a user's physiological measurements and determines the effect of the override on the user's physiological measurements in response to receiving the override signal from the interface unit 130. For example, the learning module 124 determines if the override increased or decreased the physiological measurements of the user 102, which can indicate that the user 102 has become cooler or hotter. The learning module 124 then updates the target physiological measurement information 118 with a modified target physiological measurement for a given context and any other related inputs such as controlled device operating parameters, override input information, etc.

In one embodiment, the learning module 124 performs this updating after a given number of related inputs have been received and analyzed. For example, the learning module 124 utilizes related inputs (and any output information within the received inputs) as a training set for a learning algorithm. Related inputs can be a set of inputs received by the learning module 124 that have a set of common characteristics such as similar contexts, physiological measurements, override information, etc. For example, a first input set can indicate that a user has finished exercising in the morning, has a GSR measurement of A, and set the A/C to temperature X. A second input set can indicate that a user has finished exercising in the morning, has a GSR measurement of B, and set the A/C to temperature X. A third input set can indicate that a user has finished exercising in the morning, has a GSR measurement of C, and did not change the operating parameters of the A/C. An output set for the training set can be information received as an input by the learning module 124 such as physiological measurements resulting from the user overriding current operating parameters of the controlled device and/or the new operating parameters set of the user. The learning module 124 applies one or more learning algorithms on the training set to obtain an inferred function that predicts a correct output for any valid input. The learning module 124 can use this inferred function to update the target physiological measurement information 118 with a modified target physiological measurement.

In one embodiment, the modified target physiological measurement is determined based on a value or values of physiological measurements received from the PRMs 104, 106, 108, 110 at the time the user 102 indicates that he/she is comfortable. The user 102 can indicate this by turning off the controlled device 134, manually adjusting the controlled device 134 to maintain the current environment, etc. after an override has been performed. In another embodiment, the modified target physiological measurement is determined based on an average of values of physiological measurements received from the PRMs 104, 106, 108, 110 between the time the user 102 performed an override operation and has indicated that he/she is comfortable. In yet another embodiment, the modified target physiological measurement is determined based on a value(s) or average of values of physiological measurements received from the PRMs 104, 106, 108, 110 for a given period of time after an override has been performed. Alternatively, the modified target physiological measurement is determined based on the values of the physiological measurements received from the PRMs 104, 106, 108, 110 after the physiological measurements have stabilized (e.g., have substantially finished increasing/decreasing as a result of the override). It should be noted that these are only examples of how the modified target physiological measurement is determined, and other methods are applicable as well.

FIG. 3 shows one example of modified target physiological measurements. In particular, FIG. 3 shows a table 300 comprising a first column 302 entitled "Context". This column 302 includes one or more entries identifying one or more contexts 128 such as, but not limited to, a time of day, user activities, calendar information, and the like that are to be monitored for by the context monitor 126. For example, a first entry 304 under this column 302 identifies "Context_1". Therefore, when the PRM controller 112, via the context monitor 126, detects that the context associated with "Context_1" has occurred (or is occurring), the PRM controller 112 utilizes the target physiological measurements 306, 308, 310, 312 in the row 314 corresponding to "Context_1" for the comparing and adjusting processes discussed above. FIG. 3 also shows that a second entry 316 under the first column 302 includes "N/A". This indicates that the target physiological measurements 318, 320, 322, 324 within this row 326 are to be used when a context is not detected for the comparing and adjusting processes discussed above.

In some situations an area being serviced by the controlled device 134 can be occupied by more than one individual (or animals/pets). Each of these individuals can have different comfort levels. Therefore, the PRM controller 112, in one embodiment, utilizes a weighted assessment of individual comfort to determine whether how to operate (e.g., turn on/off, keep at a current on/off state, etc.) the controlled device 134. For example, consider three entities with comfort levels a, b, c and weights w1, w2, and w3. The operating (e.g., cooling/heating) decision can be made using a formula such as $D = w1*a + w2*b + w3*c$, where, for example, w1=0.5, w2=0.25, and w3=0.25. In this example, individual "a" is given more weight in the decision D for many possible reasons such as the individual "a" is the owner of the home, is a guest, is a visitor, is ill, is old, is an infant, or has paid for a particular privilege. In some cases, "b" may represent a device that has thermal needs and, therefore, may have a relevant weighting. For example, if person "a" is comfortable, but device "b" is about to overheat, this can be considered during the thermal decision process.

The control system 101 can also be used to "make suggestions" based on a determination of user comfort level. For example, typically not all rooms in a home or rooms in a building are at the same temperature for various reasons (such as unbalanced ventilation, the presence of equipment in rooms, the direction of sunlight, outside wind directions, etc.) Therefore, the control system 101 can determine that one or more individuals are uncomfortable and make a recommendation as to an optimal room to relocate based on mathematical optimization methods. For example, the formula described above ($D = w1*a + w2*b + w3*c$) can be used by the control system 101 to make alternative room recommendations.

In some instances there can be one or more users that are using a PRM 104, 106, 108, 110 and one or more users that are not using a PRM. The control system 101 is still able to provide comfort (i.e., control the controlled device 134) for the non-PRM users by matching these users to PRM users based on previous indicated comfort levels. For example, in an office environment, an individual that does not use a PRM can utilize an interface such as, but not limited to, an application, a web page, etc. where the user can indicate his/her comfort and desired controlled device operation (cool, heat, temperature, fan speed, etc.). This application can require a login, which is used to identify the user and the user's location. Alternatively, the user is able provide his/her location. Once, the user has indicated his/her comfort and desired changes to the operation of the controlled device 134, the control system 101 identifies users in the area that are using a PRM and selects one or more of these users based on PRM markers that substantially reflect the same needs as the user without a PRM. Over time, the control system 101 can improve its accuracy by finding the best PRM user for each non-PRM user. Once identified the control system 101 can adjust the controlled device 134 for a non-PRM user by studying the PRM of the closest matching PRM user. The control system 101 can determine when to adjust the controlled device 134 for a non-PRM user by detecting entry into an area using any known method such as occupancy detection, identification card authentication, etc.

As can be seen from the above discussion, one or more embodiments increase the efficiency of a controlled device, such as an HVAC system. User comfort is also increased over a range of contexts in order to control the user's experience directly. Utilizing physiological measurements allows for a "comfort signal" to be calculated for controlling an environmental device such as an HVAC system. This saves energy by preventing unnecessary operation of the device when the user is sufficiently comfortable.

Operational Flow Diagrams

Referring now to FIGS. 4-7, the flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which includes one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 4:
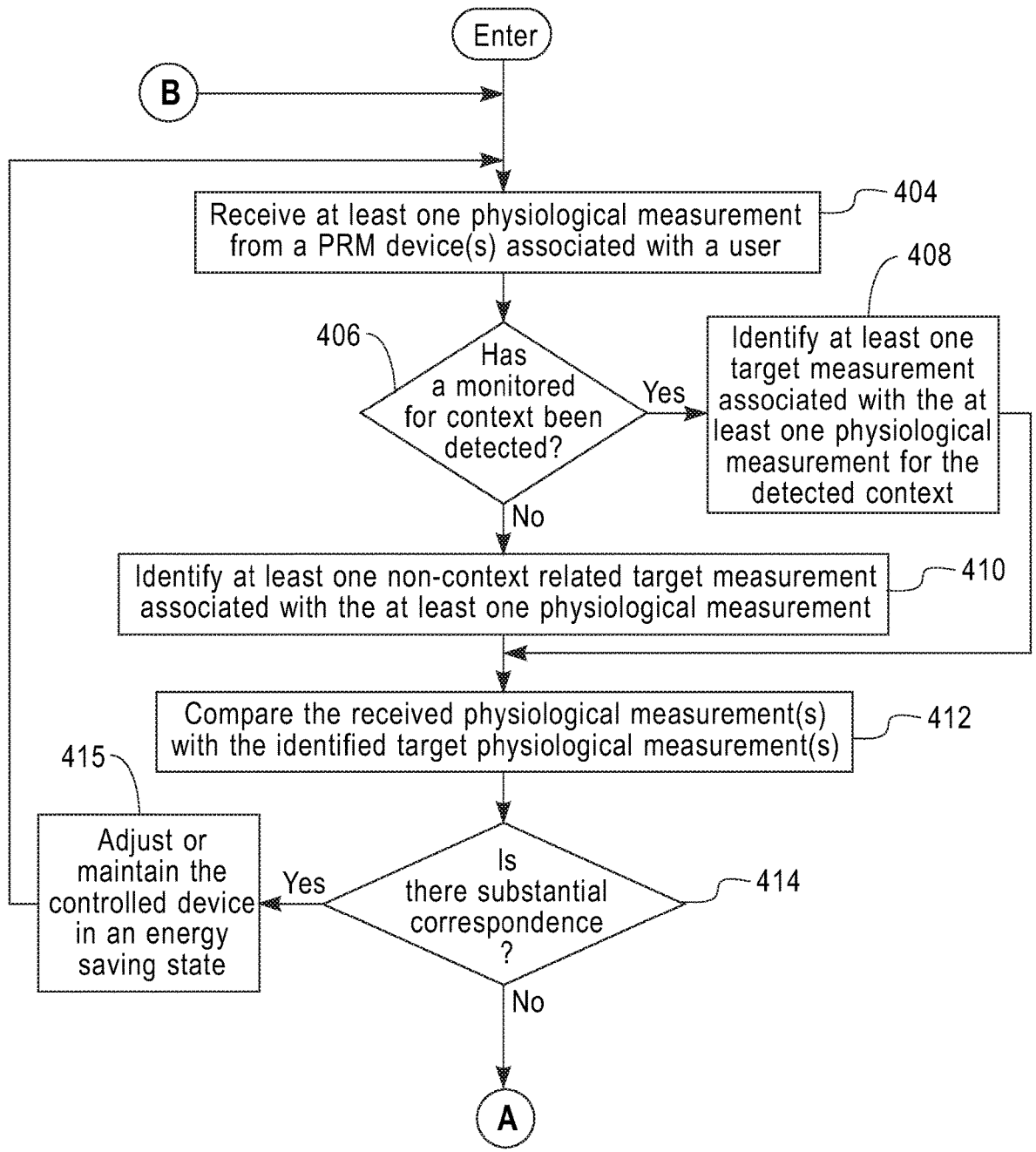
FIG. 4 is an operational flow diagram illustrating one example of a process for controlling a device based on physiological measurements associated with a user according to one embodiment of the present invention.
Figure 5:
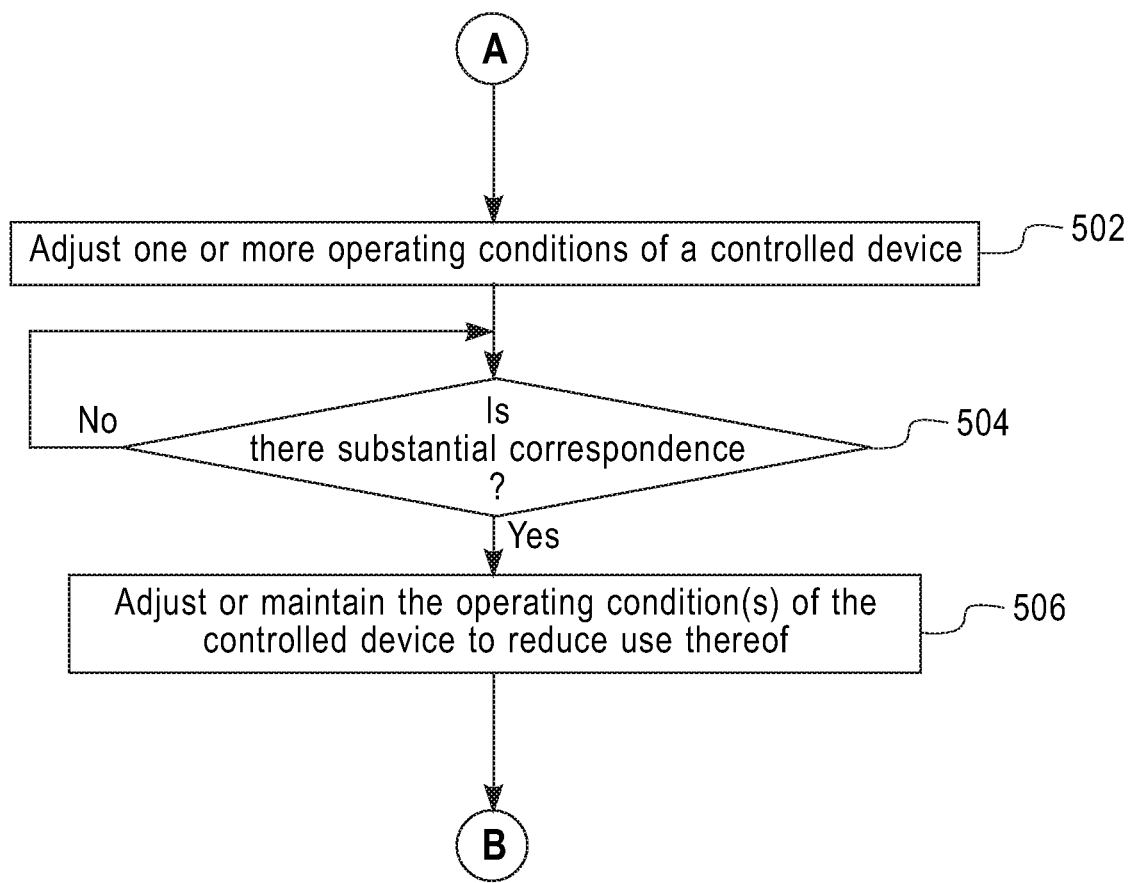
FIG. 5 is an operational flow diagram continuing the process shown in FIG. 4.

FIGS. 4-5 are operational flow diagrams illustrating one example of controlling a device based on a user's physiological measurements. The operational flow of FIG. 4 starts at step 402 and flows directly into step 404. The PRM controller 112, at step 404, receives a least one physiological measurement 116 associated with a user from one or more PRMs 104, 106, 108, 110. The PRM controller 112, at step 406, determines if a monitored for context 128 has been detected, as discussed above. If the result of this determination is positive, the PRM controller 112, at step 408, analyzes target physiological measurement information and identifies at least one target measurement 118 for the detected context that is associated with the physiological measurement(s) 116 that has been received. The control then flows to step 412.

If the result of the determination at step 406 is negative, the PRM controller 112, at step 410, analyzes target physiological measurement information and identifies at least one non-context related target measurement 118 for the physiological measurement(s) 116 that has been received. The PRM controller 112, at step 412, then compares the received physiological measurement(s) 116 with the identified target physiological measurement(s) 118, as discussed above. The PRM controller 112, at step 414, determines if there is substantial correspondence between the target physiological measurement(s) 118 and the received physiological measurement(s) 116. For example, the PRM controller 112 determines if the received physiological measurement(s) 116 substantially matches, is within, is above, is below, etc. the target physiological measurement(s) 118.

If the result of this determination is positive, the PRM controller 112, at step 415, adjusts or maintains the controlled device 134 in an energy saving state. For example, if the controlled device 134 is currently off, the PRM controller 112 keeps the device 134 in this state. In the controlled device 134 is current on, the PRM controller 112 can either turn off the device 134 of at least adjust an operating condition(s) of the device 134 so that the device operates in a mode with a higher energy savings than a previous mode. This can include changing the temperature so that the device 134 stops heating/cooling, adjusting a fan speed to a lower setting, etc. The control flow then returns to step 404. If the result of the determination at step 414 is negative, the control flows to entry point A of FIG. 5 and, at step 502, adjusts one or more operating conditions of the controlled device 134, as discussed above.

The PRM controller 112, at step 504, continues to monitor the user's physiological measurements and determines if there is a substantial correspondence between the target physiological measurement(s) 118 and the received physiological measurement(s) 116. If the result of this determination is negative, the PRM controller 112 continues monitoring the user's physiological measurements. If the result of this determination is positive, the PRM controller 112, at step 506, adjusts or maintains the operating condition(s) of the controlled device 134 to reduce its use and save energy. For example, if the controlled device 134 is currently operating, the PRM controller 112 can turn the device 134 off, reduce the fan speed, etc. If the controlled device is currently off, the PRM controller 112 can keep the device 134 turned off. The control then flows to entry point B of FIG. 4.

Figure 6:
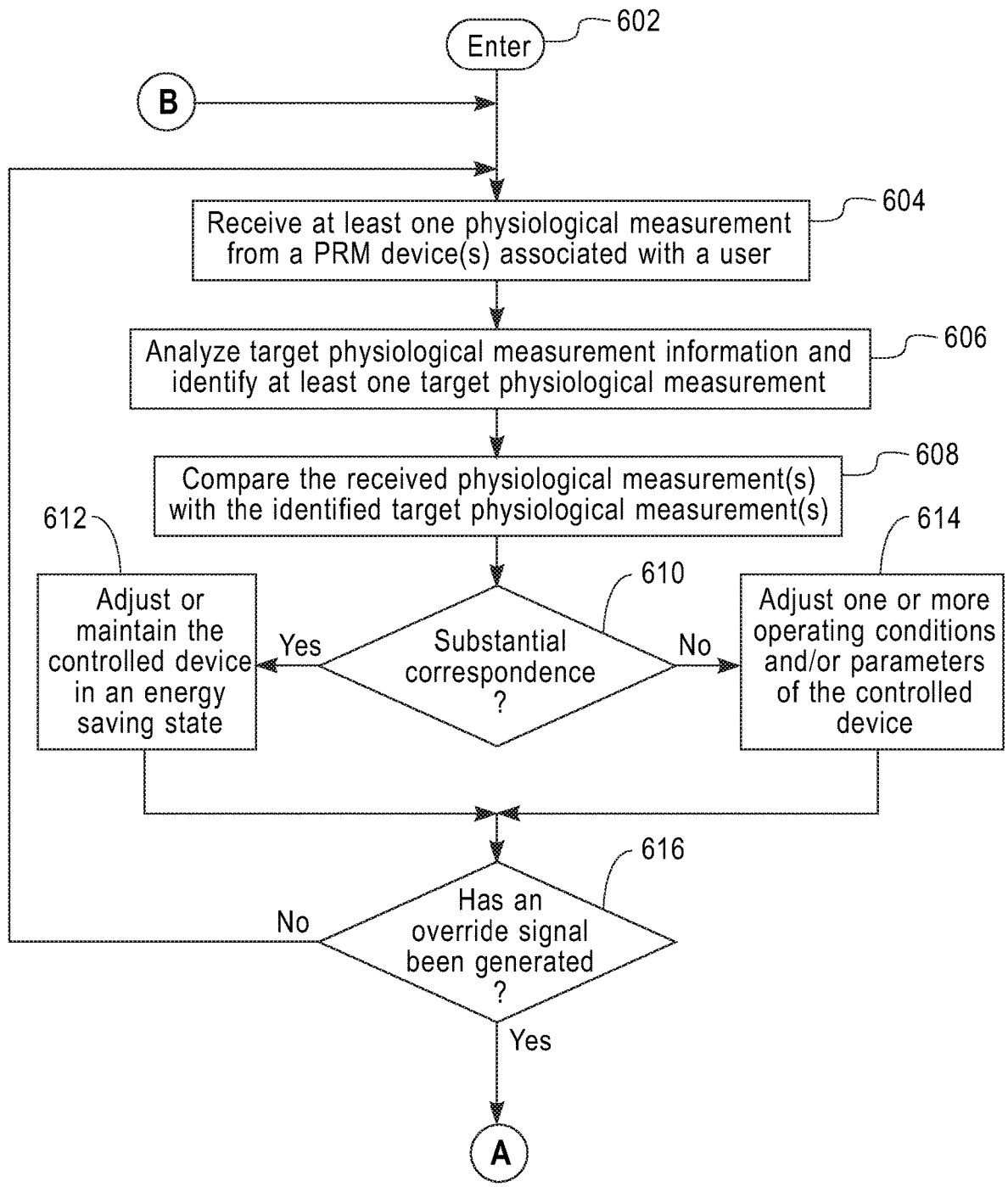
FIG. 6 is an operational flow diagram illustrating one example of a process for automatically updating target physiological measurements for a given context associated with a user according to one embodiment of the present invention.
Figure 7:
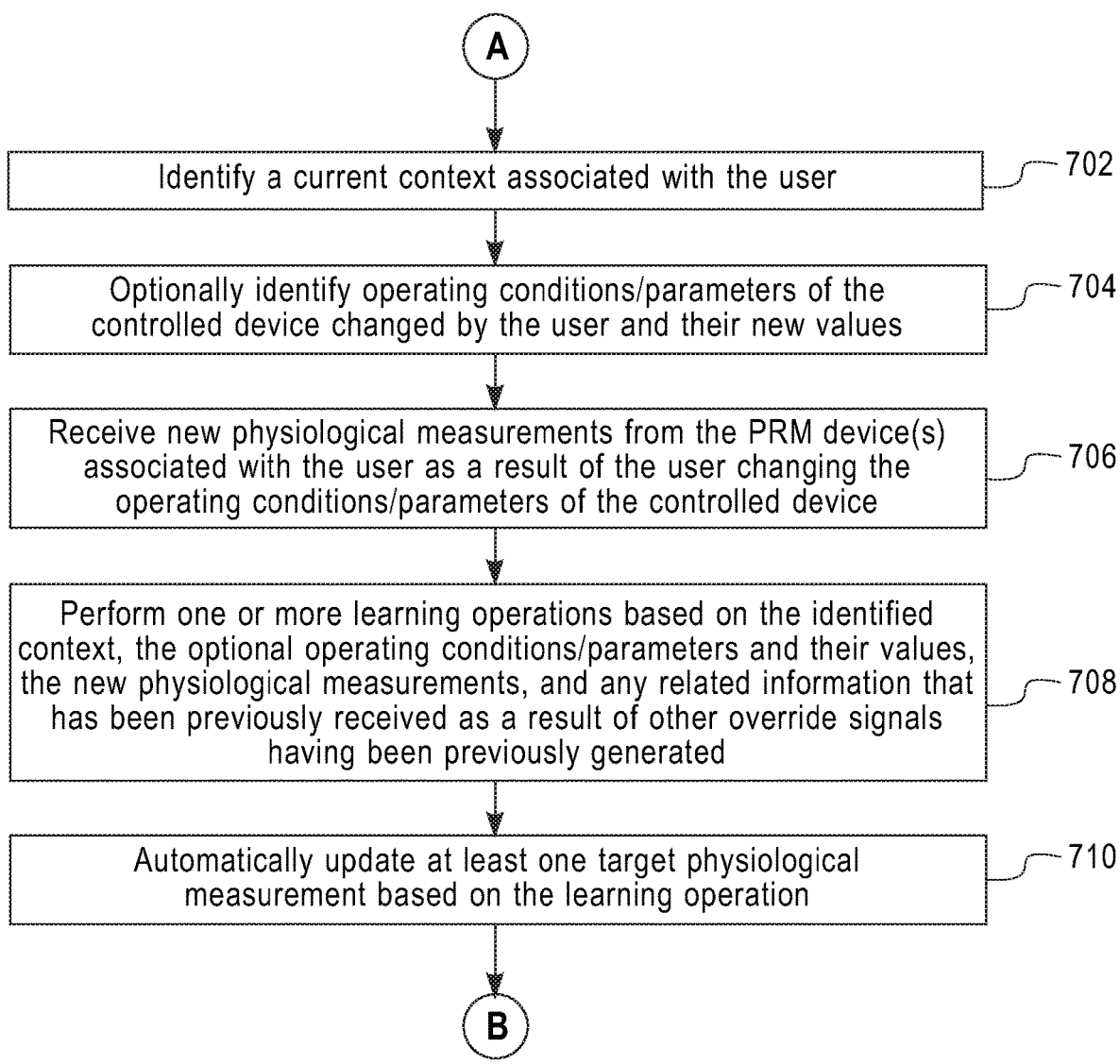
FIG. 7 is an operational flow diagram continuing the process shown in FIG. 6.

FIGS. 6-7 are operational flow diagrams illustrating one example of updating targeting physiological measurements associated with a user. The operational flow of FIG. 6 starts at step 602 and flows directly into step 604. The PRM controller 112, at step 604, receives a least one physiological measurement 116 associated with a user from one or more PRMs 104, 106, 108, 110. The PRM controller 112, at step 606, analyzes target physiological measurement information and identifies at least one target physiological measurement.

The PRM controller 112, at step 608, then compares the received physiological measurement(s) 116 with the identified target physiological measurement(s) 118, as discussed above. The PRM controller 112, at step 610, determines if there is substantial correspondence between the target physiological measurement(s) 118 and the received physiological measurement(s) 116. For example, the PRM controller 112 determines if the received physiological measurement(s) 116 substantially matches, is within, is above, is below, etc. the target physiological measurement(s) 118.

If the result of this determination is positive, the PRM controller 112, at step 612, adjusts or maintains the controlled device 134 in an energy saving state. For example, if the controlled device 134 is currently off, the PRM controller 112 keeps the device 134 in this state. In the controlled device 134 is current on, the PRM controller 112 can either turn off the device 134 of at least adjust an operating condition(s) of the device 134 so that the device operates in a mode with a higher energy savings than a previous mode. This can include changing the temperature so that the device 134 stops heating/cooling, adjusting a fan speed to a lower setting, etc. The control flow then returns to step 604. If the result of the determination at step 610 is negative, the PRM controller 112, at step 614, adjusts one or more operating conditions/parameters of the controlled device 134, as discussed above.

The PRM controller 112, at step 616, determines if an override signal has been generated. As discussed above, the override signal is generated when the user changes one or more operating conditions/parameters of the controlled device 134 that were originally set by the PRM controller 112 (or originally set by the user). If the result of this determination is negative, the control flow returns to step 604. If the result of this determination is positive, the control flows to entry point A of FIG. 7. FIG. 7 shows that in response to detecting an override signal, the PRM controller 112, at step 702, identifies a current context associated with the user, as discussed above. The PRM controller 112, at step 704, optionally identifies operating conditions/parameters of the controlled device 134 changed by the user and their new values.

The PRM controller 112, at step 706, receives new physiological measurements from the PRM device(s) associated with the user as a result of the user changing the operating conditions/parameters of the controlled device 134. The PRM controller 112, at step 708 then performs one or more learning operations based on the identified context, the optional operating conditions/parameters and their values, the new physiological measurements, and any related information that has been previously received as a result of other override signals having been previously generated, as discussed above. The PRM controller 112, at step 710, then automatically updates at least one target physiological measurement based on the learning operation. The control flow then returns to entry point B of FIG. 6.

Information Processing System

Figure 9:
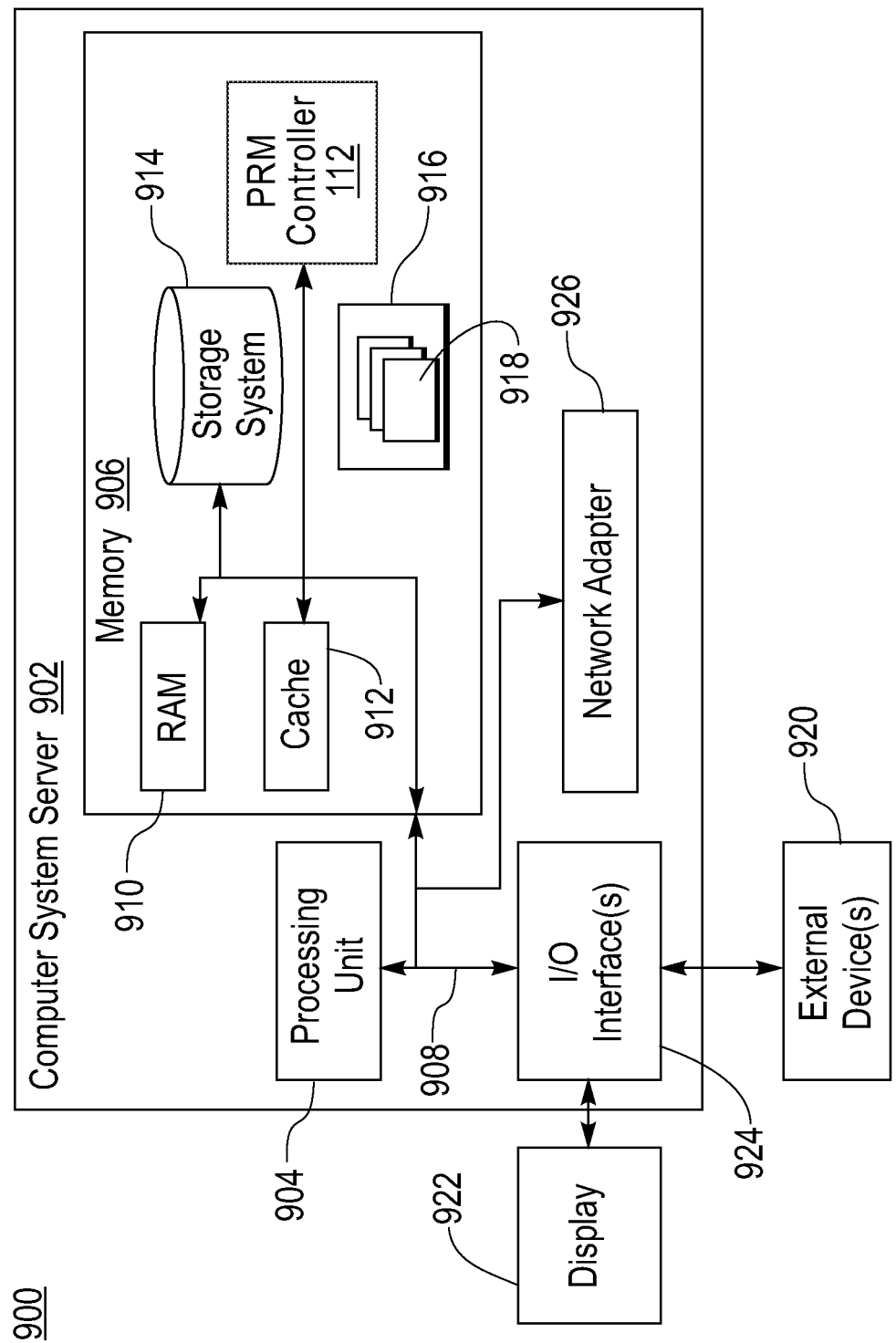

Referring now to FIG. 9, an example of an information processing system 900 such as the PRM controller 112 of FIG. 1 is shown. In information processing system 900 there is a computer system/server 902, which is operational with numerous other general purpose or special purpose computing system environments or configurations. Examples of well-known computing systems, environments, and/or configurations that may be suitable for use with computer system/server 902 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and the like.

Computer system/server 902 may be described in the general context of computer system-executable instructions, such as program modules, being executed by a computer system. Generally, program modules may include routines, programs, objects, components, logic, data structures, and so on that perform particular tasks or implement particular abstract data types.

As shown in FIG. 9, computer system/server 902 is shown in the form of a general-purpose computing device. The components of computer system/server 1902 may include, but are not limited to, one or more processors or processing units 904, a system memory 906, and a bus 908 that couples various system components including system memory 906 to processor 904. The system memory 906, in one embodiment, includes the modeling module 114, received (and optionally modeled) physiological measurements 116, target physiological measurements 118, a comparing module 120, control signal generator 122, a learning module 124, a context monitor 126, context information 128 discussed above. Each of these components can also be implemented in hardware as well. It should be noted that the node 900 can also include the interface unit 130.

Bus 908 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 902 typically includes a variety of computer system readable media. Such media may be any available media that is accessible by computer system/server 902, and it includes both volatile and non-volatile media, removable and non-removable media.

The system memory 906 can include computer system readable media in the form of volatile memory, such as random access memory (RAM) 910 and/or cache memory 912. Computer system/server 902 can further include other removable/non-removable, volatile/non-volatile computer system storage media. By way of example only, storage system 914 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 908 by one or more data media interfaces. As will be further depicted and described below, memory 906 may include at least one program product having a set (e.g., at least one) of program modules that are configured to carry out the functions of embodiments of the invention.

Program/utility 916, having a set (at least one) of program modules 918, may be stored in memory 906 by way of example, and not limitation, as well as an operating system, one or more application programs, other program modules, and program data. Each of the operating system, one or more application programs, other program modules, and program data or some combination thereof, may include an implementation of a networking environment. Program modules 918 generally carry out the functions and/or methodologies of embodiments of the invention as described herein.

Computer system/server 902 may also communicate with one or more external devices 920 such as a keyboard, a pointing device, a display 922, etc.; one or more devices that enable a user to interact with computer system/server 902; and/or any devices (e.g., network card, modem, etc.) that enable computer system/server 902 to communicate with one or more other computing devices. Such communication can occur via I/O interfaces 924. Still yet, computer system/server 902 can communicate with one or more networks such as a local area network (LAN), a general wide area network (WAN), and/or a public network (e.g., the Internet) via network adapter 926. As depicted, network adapter 926 communicates with the other components of computer system/server 902 via bus 908. It should be understood that although not shown, other hardware and/or software components could be used in conjunction with computer system/server 902. Examples, include, but are not limited to: microcode, device drivers, redundant processing units, external disk drive arrays, RAID systems, tape drives, and data archival storage systems, etc.

Non-Limiting Examples

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer implemented method for controlling a device based on physiological measurements associated with a user, the method comprising:
receiving, at an interface unit of a physiological response monitor (PRM) controller implemented with software, an override input signal generated in response to a user manually adjusting a controlled device, wherein the controlled device comprises a heating, ventilating, and air conditioning (HVAC) system;
determining that the user has manually adjusted the controlled device, based on the override input signal received at the interface unit of the PRM controller;
storing in a memory at least one target physiological measurement value associated with the user, the memory being communicatively coupled with the PRM controller;
receiving, at the PRM controller, a physiological measurement from a physiological response monitor (PRM) device physically coupled to the user to measure a physiological response of the user to one or more environmental factors including at least one of temperature, humidity, pressure, or air quality;

detecting a change, by the PRM controller, in at least one physiological measurement associated with the user, in response to the controlled device being manually adjusted, wherein the detecting a change includes comparing the at least one physiological measurement to the at least one target physiological measurement value;

modifying a target physiological measurement value associated with the user selected from the at least one target physiological measurement value associated with the user, based on the change that has been detected by the PRM controller;

comparing at least one physiological measurement associated with the user to the at least one target physiological measurement value;

determining, based on the comparing, if the at least one physiological measurement corresponds to the at least one target physiological measurement value;

adjusting at least one operating condition of the controlled device in response to the at least one physiological measurement failing to correspond to the at least one target physiological measurement value;

storing at least one additional target physiological measurement value associated with at least one additional user;

receiving at least one additional physiological measurement associated with at least one PRM device physically coupled to the at least one additional user;

identifying a first weighting metric associated with the at least one additional user;

identifying a second weighting metric associated with the user;

determining a first comfort level associated with the at least one additional user based on the at least one additional target physiological measurement value and the at least one additional physiological measurement;

determining a second comfort level associated with the user based on the at least one target physiological measurement value and the at least one physiological measurement;

calculating an optimized current state of comfort level for the user and the at least one additional user based on the first comfort level weighted by the first weighting metric and the second comfort level weighted by the second weighting metric; and adjusting at least one operating condition of the controlled device based on the optimized current state of comfort level, and a physiological measurement failing to correspond to a target physiological measurement value, wherein the physiological measurement and the target physiological measurement value are associated with at least one of the user and the at least one additional user.

2. The method of claim 1, further comprising:

detecting at least one other user indicating comfort levels and changes to the operation of the controlled device;

matching the user to the at least one other user, based on the at least one other user's previously indicated comfort levels and changes to the operation of the controlled device;

determining that the user is coupled to a physiological response monitor and the at least one other user fails to be coupled to a physiological response monitor;

determining that the at least one other user is in a location associated with the controlled device; and utilizing at least one physiological measurement associated with the user that is coupled to the physiological response monitor to control the controlled device for the at least one other user that fails to be coupled to a physiological response monitor.

3. The method of claim 1, wherein the at least one physiological measurement is at least one of:

a heart rate;

electrical activity of muscles;

a galvanic skin response; and a respiration measurement.

4. The method of claim 1, further comprising:

identifying a context associated with the user in response to determining that the user has manually adjusted the controlled device, and wherein the context is at least one of:

a time of day;

a given activity; and a scheduled calendar event.

5. The method of claim 1, wherein the target physiological measurement value is a time-varying function of a physiological measurement.

6. The method of claim 1, wherein adjusting at least one operating condition of the controlled device continues until the adjusting the at least one operating condition changes the at least one physiological measurement to correspond to the at least one target physiological measurement value.

7. The method of claim 1, wherein the at least one target physiological measurement value is the target physiological measurement value that has been modified.

8. A system for controlling a device based on physiological measurements associated with a user, the system comprising:

an interface unit communicatively coupled with a controlled device, the interface unit including an override signal monitor for detecting a user override signal generated in response to a user manually adjusting the controlled device;

a memory;

a processor communicatively coupled to the memory and the interface unit; and a physiological response monitor (PRM) controller, implemented with software, and communicatively coupled to at least one physiological response monitor (PRM) device physically coupled to a user, the interface unit, the memory, and the processor, wherein the PRM controller is configured for:

determining, based on receiving from the interface unit an override input signal at the PRM controller, that a user has manually adjusted the controlled device, wherein the controlled device comprises a heating, ventilating, and air conditioning (HVAC) system;

storing in the memory at least one target physiological measurement value associated with the user;

receiving a physiological measurement from the at least one physiological response monitor (PRM) device physically coupled to the user to measure a physiological response of the user to one or more environmental factors including at least one of temperature, humidity, pressure, or air quality;

detecting a change, by the PRM controller, in the at least one physiological measurement associated with the user, in response to the controlled device being manually adjusted, wherein the detecting a change includes comparing the at least one physiological measurement to the at least one target physiological measurement value;

modifying a target physiological measurement value associated with the user selected from the at least one target physiological measurement value associated with the user, based on the change that has been detected by the PRM controller;

comparing at least one physiological measurement associated with the user to the at least one target physiological measurement value;

determining, based on the comparing, if the at least one physiological measurement corresponds to the at least one target physiological measurement value;

adjusting at least one operating condition of the controlled device in response to the at least one physiological measurement failing to correspond to the at least one target physiological measurement value;

storing at least one additional target physiological measurement value associated with at least one additional user;

receiving at least one additional physiological measurement associated with at least one PRM device physically coupled to the at least one additional user;

identifying a first weighting metric associated with the at least one additional user;

identifying a second weighting metric associated with the user;

determining a first comfort level associated with the at least one additional user based on the at least one additional target physiological measurement value and the at least one additional physiological measurement;

determining a second comfort level associated with the user based on the at least one target physiological measurement value and the at least one physiological measurement;

calculating an optimized current state of comfort level for the user and the at least one additional user based on the first comfort level weighted by the first weighting metric and the second comfort level weighted by the second weighting metric; and adjusting at least one operating condition of the controlled device based on the optimized current state of comfort level, and a physiological measurement failing to correspond to a target physiological measurement value, wherein the physiological measurement and the target physiological measurement value are associated with at least one of the user and the at least one additional user.

9. The system of claim 8, wherein the system is further configured for:

identifying a context associated with the user in response to determining that the user has manually adjusted the controlled device, and wherein the context is at least one of:

a time of day;

a given activity; and a scheduled calendar event.

10. The system of claim 8, wherein the system is further configured for:

detecting, by the PRM controller, at least one other user indicating comfort levels and changes to the operation of the controlled device;

matching the user to the at least one other user, based on the at least one other user's previously indicated comfort levels and changes to the operation of the controlled device;

determining that the user is coupled to a physiological response monitor and the at least one other user fails to be coupled to a physiological response monitor;

determining that the at least one other user is in a location associated with the controlled device; and utilizing at least one physiological measurement associated with the user that is coupled to the physiological response monitor to control the controlled device for the at least one other user that fails to be coupled to a physiological response monitor.

11. The system of claim 8, wherein adjusting at least one operating condition of the controlled device changes the physiological measurement to correspond to the target physiological measurement value.

12. A computer program product tangibly embodying computer readable non-transitory instructions which, when implemented, cause a computer to carry out the steps of a method for controlling a device based on physiological measurements associated with a user, the computer implemented method comprising:

receiving, at an interface unit of a physiological response monitor (PRM) controller implemented with software and comprising a processor, and a memory, an override input signal generated in response to a user manually adjusting a controlled device;

determining that the user has manually adjusted the controlled device, based on the override input signal received at the interface unit of the PRM controller, and wherein the controlled device comprises a heating, ventilating, and air conditioning (HVAC) system;

storing in the memory at least one target physiological measurement value associated with the user;

receiving, at the PRM controller, a physiological measurement from a physiological response monitor (PRM) device physically coupled to the user to measure a physiological response of the user to one or more environmental factors including at least one of temperature, humidity, pressure, or air quality;

detecting a change, by the PRM controller, in at least one physiological measurement associated with the user, in response to the controlled device being manually adjusted, wherein the detecting a change includes comparing the at least one physiological measurement to the at least one target physiological measurement;

modifying a target physiological measurement value associated with the user selected from the at least one target physiological measurement value associated with the user, based on the change that has been detected by the PRM controller;

comparing at least one physiological measurement associated with the user to the at least one target physiological measurement value;

determining, based on the comparing, if the at least one physiological measurement corresponds to the at least one target physiological measurement value;

adjusting at least one operating condition of the controlled device in response to the at least one physiological measurement failing to correspond to the at least one target physiological measurement value;

storing at least one additional target physiological measurement value associated with at least one additional user;

receiving at least one additional physiological measurement associated with at least one PRM device physically coupled to the at least one additional user;

identifying a first weighting metric associated with the at least one additional user;

identifying a second weighting metric associated with the user;

determining a first comfort level associated with the at least one additional user based on the at least one additional target physiological measurement value and the at least one additional physiological measurement;

determining a second comfort level associated with the user based on the at least one target physiological measurement value and the at least one physiological measurement;

calculating an optimized current state of comfort level for the user and the at least one additional user based on the first comfort level weighted by the first weighting metric and the second comfort level weighted by the second weighting metric; and adjusting at least one operating condition of the controlled device based on the optimized current state of comfort level, and a physiological measurement failing to correspond to a target physiological measurement value, wherein the physiological measurement and the target physiological measurement value are associated with at least one of the user and the at least one additional user.

13. The computer program product of claim 12, wherein the method further comprises:

detecting at least one other user indicating comfort levels and changes to the operation of the controlled device;

matching the user to the at least one other user, based on the at least one other user's previously indicated comfort levels and changes to the operation of the controlled device;

determining that the user is coupled to a physiological response monitor and at least one other user fails to be coupled to a physiological response monitor;

determining that the at least one other user is in a location associated with the controlled device; and utilizing at least one physiological measurement associated with the user that is coupled to the physiological response monitor to control the controlled device for the at least one other user that fails to be coupled to a physiological response monitor.

14. The computer program product of claim 12, wherein adjusting at least one operating condition of the controlled device continues until the adjusting the at least one operating condition changes the at least one physiological measurement to correspond to the at least one target physiological measurement value.

* * * * *